(12) United States Patent
Bhunia

(10) Patent No.: US 8,187,198 B2
(45) Date of Patent: May 29, 2012

(54) RAPID THERMAL DETECTION OF CARDIAC OUTPUT CHANGE

(75) Inventor: Sourav Bhunia, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 450 days.

(21) Appl. No.: 12/421,359

(22) Filed: Apr. 9, 2009

(65) Prior Publication Data

US 2009/0198143 A1    Aug. 6, 2009

Related U.S. Application Data

(62) Division of application No. 11/674,901, filed on Feb. 14, 2007, now Pat. No. 7,563,231.

(51) Int. Cl.
*A61B 5/02* (2006.01)
(52) U.S. Cl. ........................................ 600/505; 600/504
(58) Field of Classification Search .................. 600/504, 600/505, 526
See application file for complete search history.

(56) References Cited

U.S. PATENT DOCUMENTS 4,841,981 A * 6/1989 Tanabe et al. ................. 600/505
5,860,922 A * 1/1999 Gordon et al. ................ 600/431

* cited by examiner

*Primary Examiner* — Patricia Mallari
*Assistant Examiner* — Christian Jang
(74) *Attorney, Agent, or Firm* — Reed A. Duthler; Stephen W. Bauer; Evans M. Mburu

(57) ABSTRACT

An improved system for measuring changes in blood flow, particularly in the context of an automatic arrhythmia treatment device. The system includes a heater, exposable to a bloodstream, a driver providing power to the heater, a temperature sensor, isolated from the blood stream and thermally coupled to the temperature of the heater and a measurement circuit coupled to the temperature sensor, providing signals indicative of blood flow. The system may include an intravascular lead having a lead body wherein the heater is mounted to the lead body so as to dissipate its generated heat into the blood. The heater and temperature sensor may be thermally insulated from the lead body and the heater and the temperature sensor may be on substantially a single isotherm during operation.

4 Claims, 3 Drawing Sheets

RAPID THERMAL DETECTION OF CARDIAC OUTPUT CHANGE

CROSS-REFERENCE TO RELATED APPLICATIONS

This application is a divisional of U.S. patent application Ser. No. 11/674,901 filed on Feb. 14, 2007. The disclosure of the above application is incorporated herein by reference.

FIELD OF THE INVENTION

This invention relates to arrhythmia detection and treatment generally and more particularly to detection and treatment of tachyarrhythmias using implantable stimulators.

BACKGROUND OF THE INVENTION

In the context of treating rapid ventricular tachycardias, it is useful to be able to determine whether the rapid rate is accompanied by a substantial drop in cardiac output. If so, a cardioversion or defibrillation level shock may be required. If not, pacing therapies may be usefully applied, at least initially. As high level shocks are painful, patients generally prefer to avoid their unnecessary application.

To this end, it has been proposed to incorporate hemodynamic sensors of various sorts into automatic implantable cardioverter defibrillators (ICDs), to allow the devices to deliver the most appropriate therapies. One approach has been to measure intravascular blood flow as an indicator of cardiac output, i.e. low flow implies low output. Such devices are generally disclosed in U.S. Pat. No. 5,782,879 issued to Rosborough, et al., U.S. Pat. No. 5,520,190 issued to Benedict, et al. and U.S. Pat. No. 5,409,009, issued to Olson, all of which are incorporated herein by reference in their entireties.

While not employed in the above-cited patents, it is also known that cardiac output and blood flow can be measured by determining the result of heat by means of an intravascular heater. In general, the more blood flow, the greater the dissipation of heat from the heater. Exemplary devices are disclosed in U.S. Pat. No. 6,387,052, issued to Quinn, et al and US Patent Application Publication No. US2003/0225336 A1, by Callister, et al., both of which are also incorporated herein by reference in their entireties.

SUMMARY

The present invention is directed to an improved method and apparatus for measuring changes in blood flow in the context of an automatic arrhythmia treatment device. In some embodiments, the invention may employ a flow sensor which is activated in response to detection of a tachyarrhythmia or in response to delivery of an anti-tachyarrhythmia therapy. If activated in response to detection of tachyarrhythmia, the flow sensor may be employed to determine whether a substantial drop in cardiac output has or has not occurred, in order to select an appropriate therapy, in particular to avoid unnecessary delivery of high level shocks. If activated in response to delivery of an anti-tachyarrhythmia therapy, the flow sensor may be employed to determine whether the therapy was or was not successful in correcting a low cardiac output or whether a reduced cardiac output followed delivery of the therapy.

In some embodiments, the flow sensor may be employed to determine a first reference flow measurement under known conditions of normal cardiac output and a second reference flow measurement under conditions of known cardiac hemodynamic compromise, i.e. during unstable ventricular tachycardia or ventricular fibrillation. Flow measurements taken using the sensor may be compared to these reference measurements to determine whether cardiac output has been substantially reduced.

In some embodiments, the flow sensor takes the form of a heater, exposed to intravascular blood flow and thermally coupled to a temperature sensor responsive to the temperature of the heater. The heater may be an electrically powered by a driver providing a signal of constant voltage, current or power, with the temperature sensor providing an output signal proportional to the temperature of the heater. Generally, the higher the temperature of the heater, the lower the blood flow. In this embodiment, the sensor is particularly desirable for long-term intravascular implant, as over time, changes in sensor response due to fibrous encapsulation can be addressed. As the sensor is not employed to derive an actual measurement of cardiac output but only a change in output, shifts in the reference measurements for normal cardiac output and hemodynamic compromise can be taken account of. In the context of the present invention, only relative changes in cardiac output, not precise measurements of cardiac output are needed. Since only a change in the cardiac output is intended to be measured here, a miniature heater may be used that is substantially smaller than what is used for the measurement of the actual magnitude of the blood flow rate. Also an analysis of the temperature transient during powering up of the heater may be employed to determine a change the blood flow rate with respect to its predetermined reference level.

DETAILED DESCRIPTION OF THE ILLUSTRATED EMBODIMENTS

Figure 1:
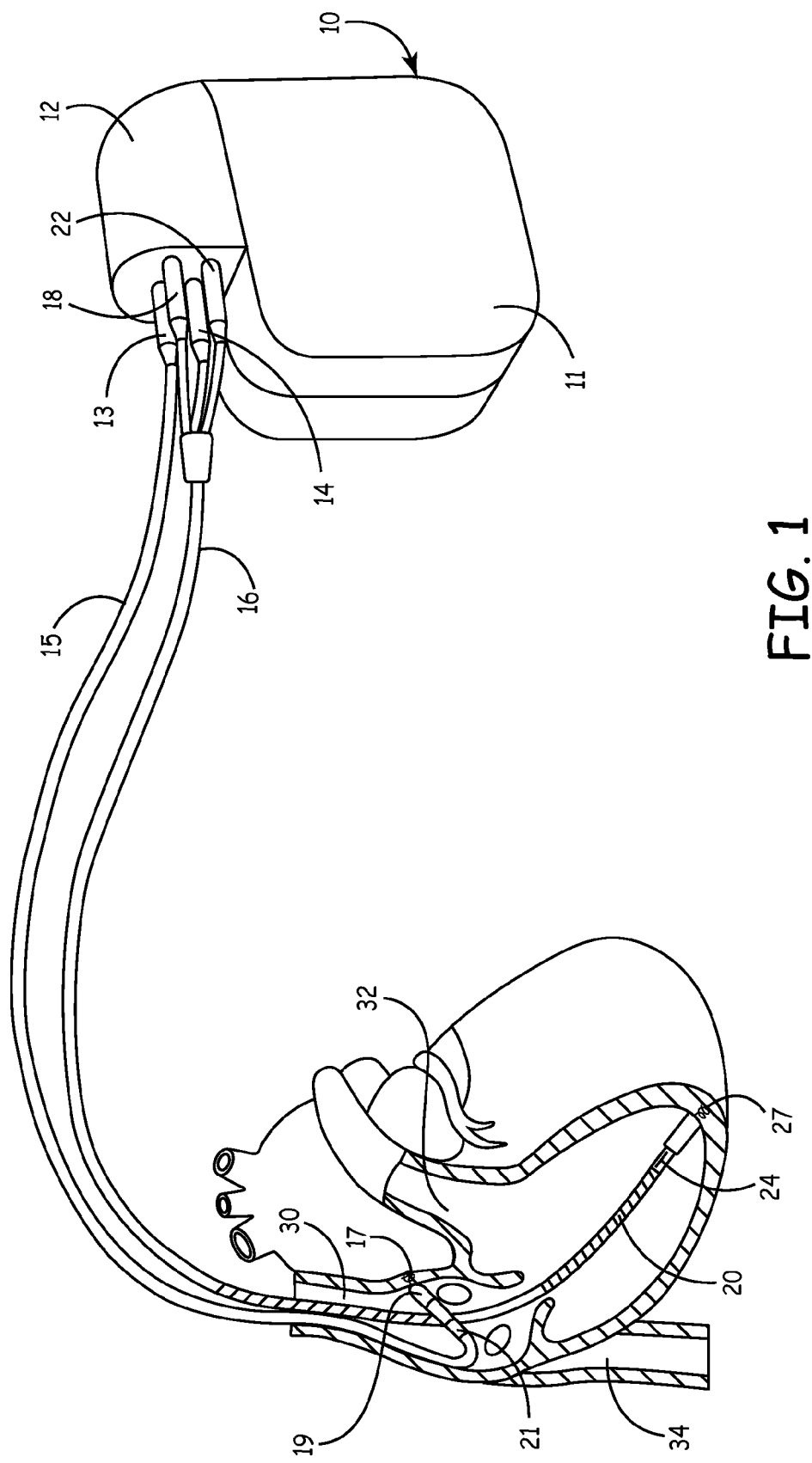
FIG. 1 a depiction of an exemplary device in which the invention may be practiced, in this case an ICD, shown as connected to a patient's heart.

FIG. 1 illustrates an ICD 10 appropriate for use in practicing the present invention. The device may generally correspond to that described in the ICD patents referenced above or more particularly to that described in U.S. Pat. No. 5,545,186, issued to Olson, et al, also incorporated herein by reference in its entirety. However, the invention is believed useful in conjunction with any of the various ICD platforms presently available. The device is provided with a conductive, hermetic enclosure 11, which may serve as a return electrode for cardioversion/defibrillation pulses and pacing pulses delivered by the lead system as well as a sensing electrode. A connector block 12 serves to interconnect the ICD to the lead system using any of the known connector configurations. The lead system as illustrated would be used in an ICD suitable for dual chamber pacing and treatment of ventricular tachyarrhythmias. However, the invention would also be useful in devices having only ventricular pacing and sensing or combined atrial and biventricular pacing and sensing, as well as for devices capable of treating atrial tachyarrhythmias.

The lead system as illustrated includes an atrial pacing/sensing lead 15, carrying two electrodes 19 and 21, connected to the ICD 10 by means of a connector 13 inserted in connector block 12. The lead system also includes a ventricular pacing/cardioversion/defibrillation lead 16 carrying a defibrillation electrode 20 and a single or a pair of pacing and sensing electrodes 27, located at its distal portion, including the tip. These electrodes are connected to ICD 10 by means of connectors 18 and 22, inserted in connector block 12. Lead 16 also carries a flow sensor 24 appropriate for use in conjunction with the present invention. Sensor 24 is connected to ICD 10 by means of a connector 14 inserted in connector block 12. In the particular embodiment of sensor 24 described below, the sensor requires three or four mutually insulated conductors, so connector 14 would preferably be a tri- or quadripolar, in-line connector.

As illustrated, sensor 24 is located in the right ventricle on a cardioversion/defibrillation lead. However, it may also be located in the superior vena cava 30, the inferior vena cava 34 or the right ventricular outflow tract 32. While the sensor is shown as mounted to a cardioversion/defibrillation lead, it may also be mounted to a pacing lead such as lead 15, or on a separate lead carrying only the sensor.

Figure 2:
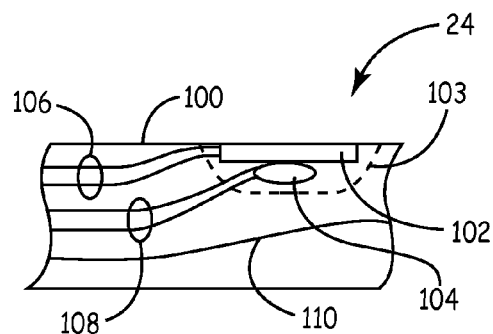
FIG. 2 is a schematic illustration of a flow sensor useful in practicing the present invention.

FIG. 2 is a schematic diagram of an embodiment of sensor 24, as it might be located in the body 100 of a pacing or cardioversion/defibrillation lead such as lead 16 (FIG. 1). The sensor comprises a heater 102 and a temperature sensor 104 thermally coupled to the heater. The heater 102 may be a thin film resistive heater; however other available heaters may be employed. Whatever heater is chosen, it is desirable that it can perform measurement cycles as discussed below with an energy expenditure of about one Joule or less to minimize battery drain on the associated ICD. Temperature sensor 104 may simply be a thermistor, but other alternative known temperature sensors might be substituted. The temperature sensor and the heater shall be in close thermal contact by being in direct contact with one another or by having minimal thermal resistance between them, ideally by being on substantially the same isotherm. Also, both the heater and the temperature sensor shall be thermally insulated from the physical platform they are mounted on, such as the pacing and the cardioversion/defibrillation lead, such that the heat generated by the heater is dissipated preferably entirely or at least substantially into the surrounding blood stream. A thermally insulating material 103 such as non-conductive epoxy, silicone, polyurethane, fiberglass, or other suitable materials may be employed to isolate the sensor from the body 100 of the lead. Temperature sensor 104 provides a temperature signal to the ICD over mutually insulated conductors 108. If sensor 104 is a thermistor, the output signal will be a variable voltage drop or a variable current level in an electrical current applied across the thermistor by conductors 108. Also illustrated is an additional conductor 110, which may be, for example the conductor coupled to pacing electrode 27 (FIG. 1.)

Since only a change in the blood flow rate is to be measured here as opposed to the actual magnitude of the blood flow rate, a miniature heating element may be adequate. This makes the sensor suitable for integration with chronically implantable intracardiac leads of an ICD or a pacemaker.

Figure 3:
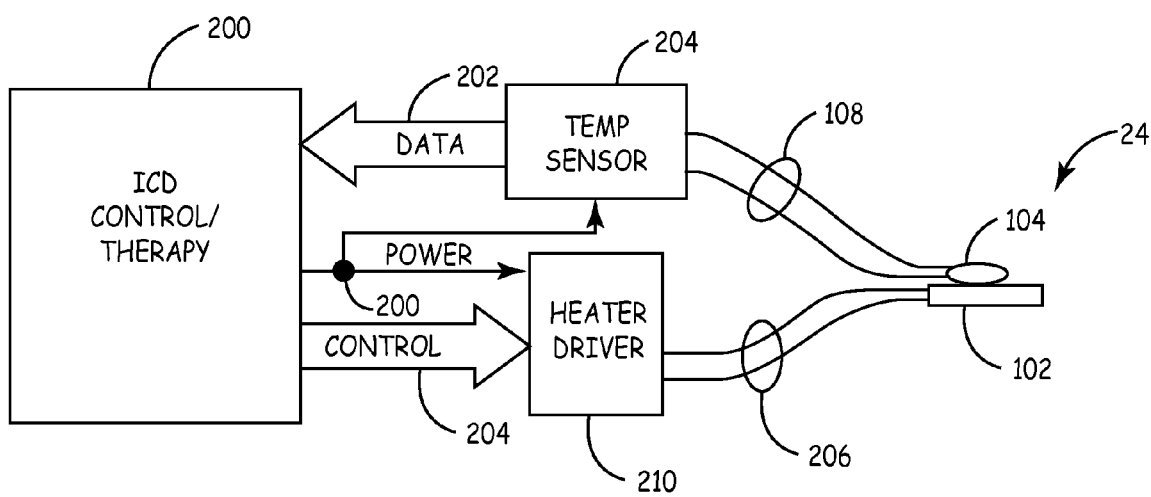
FIG. 3 is a schematic diagram illustrating the functional interconnection of a sensor as in FIG. 2 with an ICD as in FIG. 1

FIG. 3 is a block schematic diagram illustrating the interconnection of an ICD, such as that illustrated in FIG. 1 with a sensor appropriate for use in the present invention, such as that illustrated in FIG. 2. The ICD contains control/therapy delivery circuitry which may correspond generally to any of the various available ICD platforms. The operation of the circuitry 200 is controlled by a processor therein, under control of stored software. These devices typically also include RAM memories which may be used to store measured physiological parameters, and which in the context of the present invention are also used to store measurements from sensor 24. The circuitry 200 will also typically include a battery which powers the ICD and a set of high voltage capacitors, used to deliver high voltage cardioversion and defibrillation shocks. Either source may be used to power the heater 102 via heater drive 210. However, it is believed, especially if the sensor is activated following delivery of a high voltage shock, that battery savings could be obtained by employing residual charge stored in the capacitors to power the heater 102.

Sensor 24 is activated under control of the processor in circuitry 200 at various times. Power to sensor driver 210, which in preferred embodiments may be a constant voltage, constant current or constant power electrical source, is delivered on line 200. Power is delivered to heater 102 via conductors 106. The time duration of activation is controlled by control bus 208, according to instructions from the processor in the circuitry 200. The temperature signal from sensor 24, in the embodiment in which the temperature sensor 104 is a thermistor, will be a measured voltage drop or current change across conductors 108, as sensed by temperature sensor circuitry 204. This value may be digitized by sensor circuitry 204 and provided to the processor in circuitry 200 on data bus 202 or alternatively may be provided to an A/D converter in circuitry 202, if present. If temperature sensor 104 is a thermistor, circuitry 200 will need to provide a low level electrical signal to sensor circuitry 204 via line 206, in order to allow the temperature measurement to be made. In the case of the invention being practiced in the context of an ICD, temperature sensing circuitry and the heater driver will preferably be located within the hermetic enclosure of the ICD.

In operation, the sensor 24 may be activated at various times and for various purposes. These operations are discussed in more detail in conjunction with the flow chart of FIG. 4, below.

Figure 4:
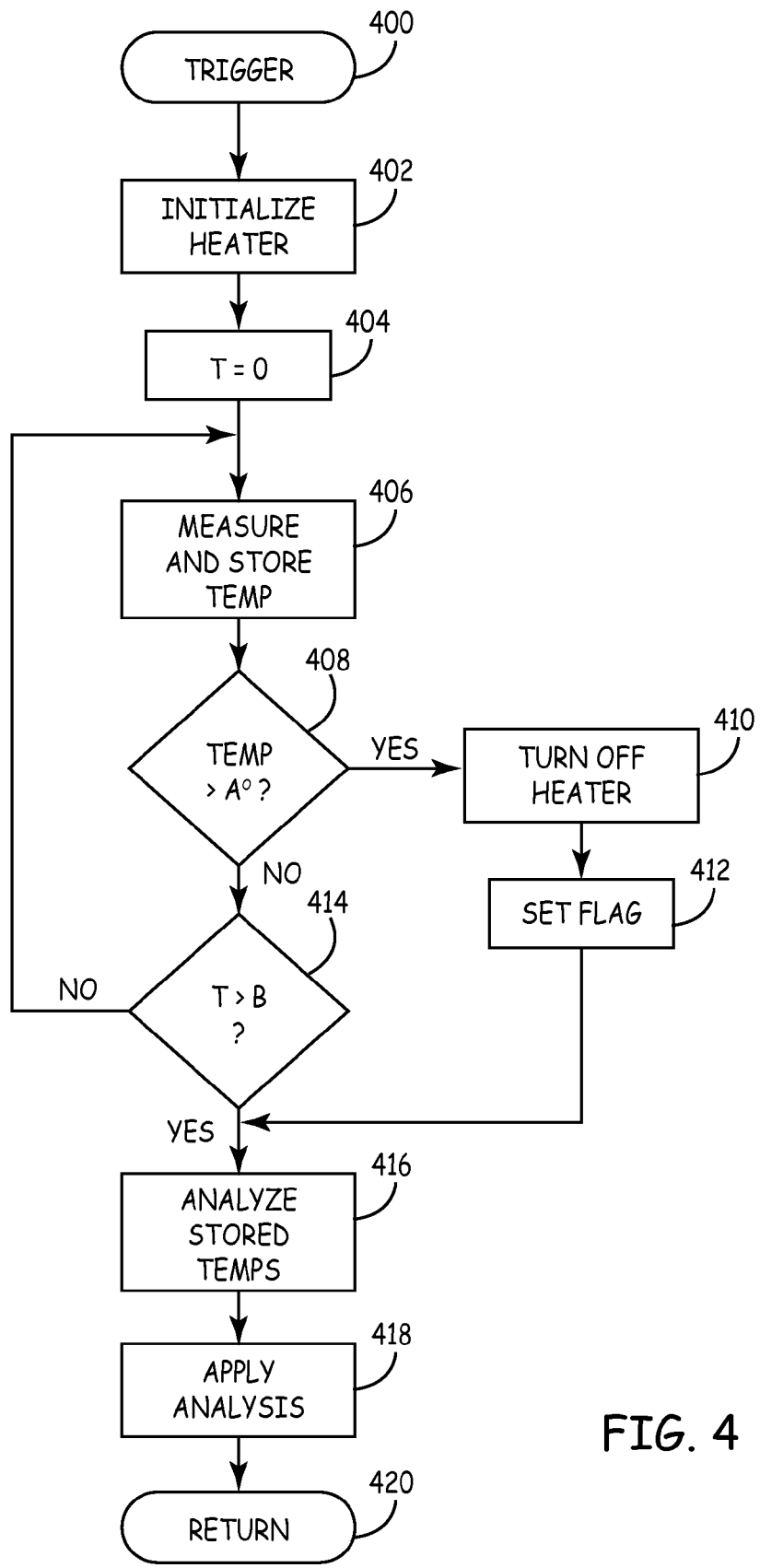
FIG. 4 is a functional flow chart illustrating operation of a sensor according to the present invention in as used in conjunction with the present invention.

FIG. 4 is a functional flow chart illustrating various operations of a sensor according to the present invention in conjunction with an automatic tachyarrhythmia detection and treatment device, such as the ICD illustrated in FIG. 1. In order to initialize the operation of the sensor, it may be desirable to acquire reference values, including a first reference flow measurement taken during periods of known normal heart rhythm and a reference flow measurement taken during a period of known hemodynamic compromise (substantially reduced cardiac output), such as during very high rate ventricular tachycardias or fibrillation.

The first reference flow measurement will likely be taken while the ICD is under control of a physician, by means of an external programmer. Subsequent measurements may be taken automatically at infrequent interval, triggered by the processor in the ICD circuitry 200 (FIG. 3), during periods of detected normal heart rate. In either case, in response to a trigger at 400 from the processor in ICD circuitry 200, the heater driver 210 (FIG. 3) will activate the heater for a short transient period sufficient for the heater to reach a fully "on" condition at 402. The processor will then initialize a time interval "T" at 404, which defines the measurement duration. Preferably this interval is as short as practical to minimize drain on the ICD's batteries, but the time interval should be long enough to include at least one and preferably multiple cardiac cycles. The duration of interval T therefore may be defined as a function of the heart rate sensed by circuitry 200. During interval T, the processor will repetitively sample the temperature signal derived from sensor 24 (FIG. 2) and store the measured values. This process will continue until expiration of T at 414 or until the temperature exceeds a safe value "A", e.g. 43 degrees centigrade at 408. If the temperature exceeds the safe level A at 408, the heater is turned off and a flag is set at 412 to indicate that the heater has exceeded its safe temperature.

After temperature measurement ceases, the stored temperatures are analyzed at 416 and the analysis is applied to control the operation of the ICD. In the event that the measurement cycle is completed successfully it can be used to set a baseline first reference value indicative of normal heart rate. At 418 and the ICD may return to its normal operative mode at 420. Optionally, several temperature measurement cycles mat be performed and an average or composite reference value derived. In the event that the temperature exceeds safe values at 408, the processor may determine not to use the sensor at 418 or may instruct the heater driver circuit 210 to reduce its drive signal and restart the measurement process. In the event that the trigger signal at 400 is intended to acquire a second reference value indicative of hemodynamic compromise, the device operates exactly as described above, with the exception that the stored reference value is indicative of hemodynamic compromise rather the normal cardiac output. In this case, however, it is anticipated that any updating of the second reference value will occur under control of the physician rather than automatically by the ICD. In an alternative embodiment, the excursion of the heater temperature beyond a safe level might itself be employed as an indicator of hemodynamic compromise. However, this is believed to be a less preferred embodiment.

The trigger signal at 400 may also be provided in response to detection of a tachyarrhythmia or after delivery of an antitachyarrhythmia therapy. In either case, the measurement cycle proceeds as discussed above. However at 416 the analysis performed is to determine whether the measured values more closely resemble the first baseline reference or the second, hemodynamic compromise reference. This analysis may comprise comparisons of average or maximum values received from the temperature sensor during the measurement cycle or may employ comparisons of peak slope or other more complex digital signal analysis techniques.

In an alternative embodiment, the step at 402 of waiting for the sensor to reach a fully "on" condition may be omitted and measurements of temperature signal during the transient period after the heater is turned on may be employed. For example, one analysis of the blood flow rate change may involve calculation of the slope or the rate of temperature rise at two sufficiently separated instants of time during the temperature transient after the heater is powered on. The logarithm of the ratio of those two slopes is proportional to the velocity of blood flow surrounding the sensor. This quantity is to be compared with its corresponding baseline value to determine any substantial change in the blood flow rate.

In the event the measurement is triggered in response to detection of a tachyarrhythmia, the processor in circuitry 200 (FIG. 3) may employ it to select between pacing level therapies and high energy therapies, depending on whether hemodynamic compromise was detected. If the measurement cycle was triggered following delivery of a therapy, the processor in circuitry 200 (FIG. 3) may use the result to determine whether the previously delivered therapy should be repeated or altered.

The invention claimed is:

1. An intravascular blood flow sensor system, comprising:
a heater, exposable to a bloodstream;
a driver providing power to the heater;
a temperature sensor, isolated from the bloodstream and thermally coupled to and responsive to the temperature of the heater;
a measurement circuit coupled to the temperature sensor, providing signals indicative of blood flow as a function of signals from the temperature sensor; and
wherein the heater and temperature sensor are thermally insulated from the lead body; and
wherein the system comprises an intravascular lead having a lead body and wherein the heater is mounted to the lead body so as to dissipate its generated heat into the blood.

2. A system according to claim 1 wherein the heater and the temperature sensor are on substantially a single isotherm during operation.

3. An intravascular blood flow sensor system, comprising:
a heater, exposable to a bloodstream;
a driver providing power to the heater;
a temperature sensor, isolated from the bloodstream and thermally coupled to and responsive to the temperature of the heater;
a measurement circuit coupled to the temperature sensor, providing signals indicative of blood flow as a function of signals from the temperature sensor; and
wherein the measurement circuit provides signals indicative of slopes of the signals from the temperature sensor.

4. An intravascular blood flow sensor system, comprising:
a heater, exposable to a bloodstream;
a driver providing power to the heater;
a temperature sensor, isolated from the bloodstream and thermally coupled to and responsive to the temperature of the heater;
a measurement circuit coupled to the temperature sensor, providing signals indicative of blood flow as a function of signals from the temperature sensor;
wherein the measurement circuit provides signals indicative of slopes of the signals from the temperature sensor; and
wherein the measurement circuit provides signals indicative of slopes of the signals from the temperature sensor after transient periods following activations of the sensor.

* * * * *